United States Patent [19]
Reinhold, Jr.

[11] Patent Number: 5,339,823
[45] Date of Patent: Aug. 23, 1994

[54] TWELVE-LEAD PORTABLE HEART MONITOR AND METHOD

[75] Inventor: Herbert E. Reinhold, Jr., Rockville, Md.

[73] Assignee: Survival Technology, Inc., Rockville, Md.

[21] Appl. No.: 925,912

[22] Filed: Aug. 7, 1992

[51] Int. Cl.$^5$ .......................................... A61B 5/0404
[52] U.S. Cl. .................................. 128/710; 128/696; 128/904
[58] Field of Search ............... 128/710, 696, 639, 640, 128/644, 904

[56] References Cited

U.S. PATENT DOCUMENTS

| | | |
|---|---|---|
| 3,058,458 | 10/1962 | Daneman . |
| 3,776,228 | 12/1973 | Semler ................... 128/710 |
| 3,792,700 | 2/1974 | Sarnoff et al. . |
| 3,910,260 | 10/1975 | Sarnoff et al. . |
| 3,938,507 | 2/1976 | Sarnoff et al. . |
| 4,004,577 | 1/1977 | Sarnoff . |
| 4,318,412 | 3/1982 | Stanly et al. .......... 128/696 |
| 4,573,474 | 3/1986 | Scibetta ............... 128/696 X |
| 4,608,987 | 9/1986 | Mills .................... 128/639 |
| 4,658,830 | 4/1987 | Sarnoff . |
| 4,763,660 | 8/1988 | Kroll et al. ............ 128/640 |
| 4,862,896 | 9/1989 | Reinhold, Jr. et al. . |
| 4,889,134 | 12/1989 | Greenwold et al. . |
| 4,957,109 | 9/1990 | Groeger et al. ......... 128/696 X |
| 5,224,479 | 7/1993 | Sekine .................. 128/644 |

FOREIGN PATENT DOCUMENTS 8909020 10/1989 World Int. Prop. O. .......... 128/696

*Primary Examiner*—Lee S. Cohen
*Assistant Examiner*—Jeffrey R. Jastrzab
*Attorney, Agent, or Firm*—Cushman, Darby & Cushman

[57] ABSTRACT

A method and device for obtaining electrical heart activity of an individual in a form capable of producing a twelve-lead electrocardiogram of an individual. The device includes a portable electrode support having an array of six non-adhesive precordial electrodes fixed thereon at predetermined positions within the array which correspond with the Wilson precordial leads for the individual. The device also includes a right arm electrode, a left arm electrode, a left leg electrode and circuitry for converting the electrical heart activity of the individual obtained by said electrodes into a form capable of producing a twelve-lead electrocardiogram. The method includes the steps of applying the left leg, left arm and right arm electrode to the skin of the individual at locations such that the circuitry can be electrically operable to obtain leads I, II, III, AVR, AVL, and AVF therefrom. Human pressure is applied to engage the array of six precordial electrodes with the skin of the chest of the individual in an operative relation, and circuitry is operated for a time sufficient to obtain electrical heart activity of the individual in a form capable of producing an electrocardiogram.

33 Claims, 3 Drawing Sheets

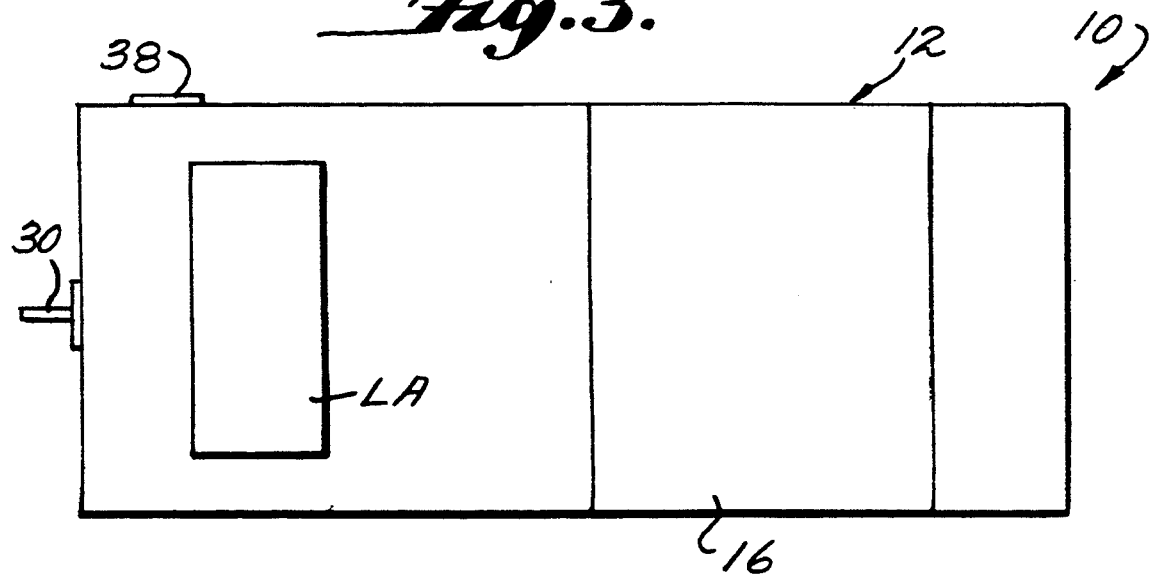
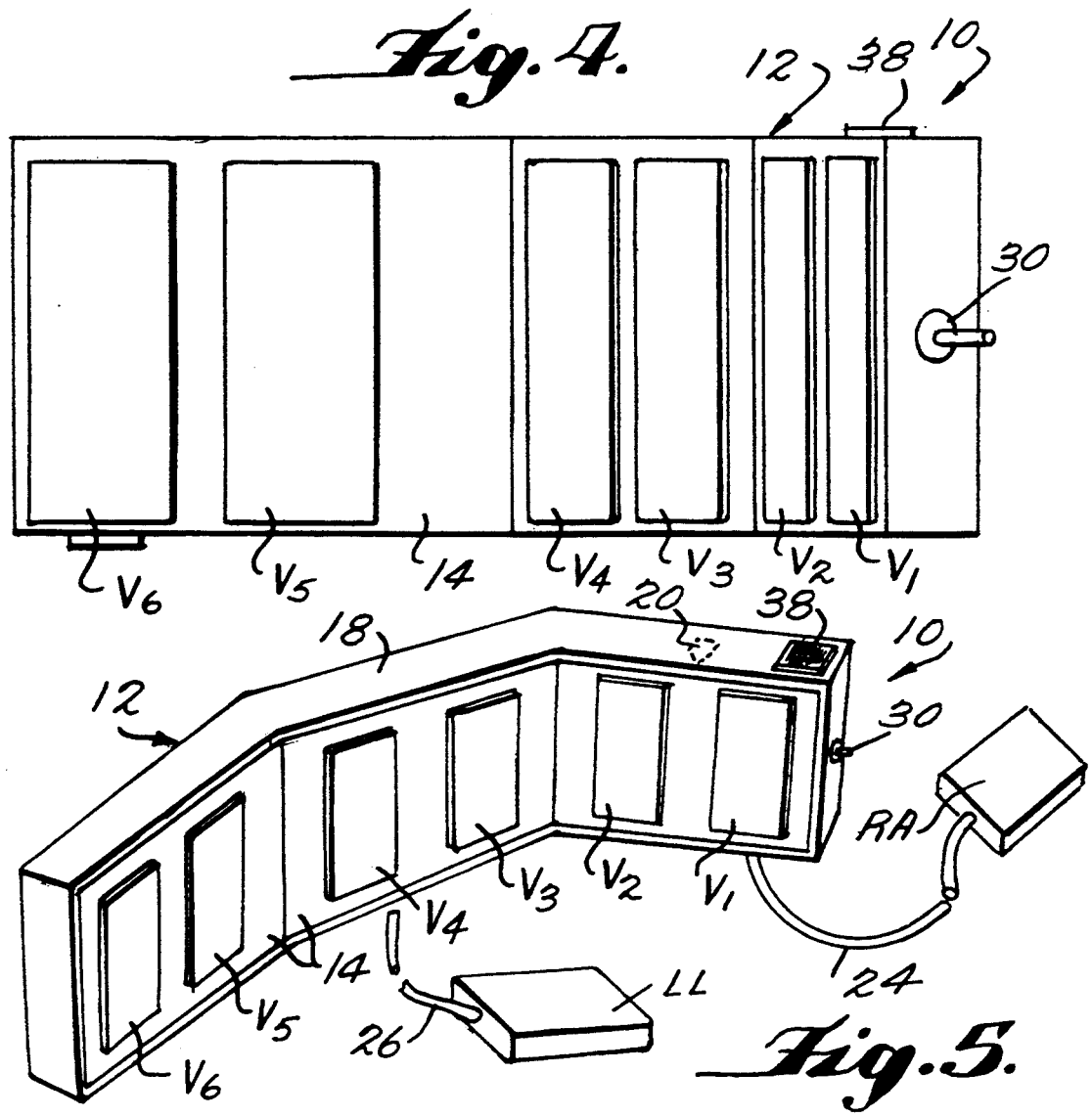

5,339,823

TWELVE-LEAD PORTABLE HEART MONITOR AND METHOD

BACKGROUND OF THE INVENTION

This invention relates to heart monitors and more particularly to heart monitors of the portable type.

One example of a portable heart monitor of the type herein contemplated is disclosed in commonly assigned U.S. Pat. No. 3,938,507. The monitor of the '507 patent is provided with a pair of electrodes which are configured so as to be conveniently and comfortably held within the armpits of a user in accordance with the teachings of U.S. Pat. No. 3,792,700. The preferred use of the device is in the method disclosed in U.S. Pat. Nos. 3,910,260, 4,004,577, and 4,658,830. As disclosed in the aforesaid patents, heart monitors may be used in conjunction with medicaments contained within autoinjectors for enabling a designated coronary-prone individual to self-administer arrhythmia and thrombolytic treatment drugs during the early minutes or hours of the onset of heart attack symptoms at a time before the individual can be hospitalized or reached by an ambulance crew. For this use, it is important that the monitor be capable of simple, but effective, connection with the user so as to acquire the electrical activity of the heart of the user in a form capable of transmission over a telephone line to a central source where sufficient intelligence is provided for aiding the individual in undertaking the self-administered treatment.

Portable heart monitors are also utilized as portable diagnostic tools. For this purpose, the emergency utilization of the device is not as critical as in the use described above. Typically, a portable heart monitor could be used by paramedics to monitor the heart of a patient which is being transported to the hospital. In addition, such portable monitors are quite useful in physician house calls. Moreover, portable monitors can have many uses in hospitals as well.

A limitation on the two-electrode monitor disclosed in the aforesaid '507 patent is that it is capable essentially of providing only one lead out of the twelve leads which are conventionally provided by non-portable in hospital ECG machines, see, for example, U.S. Pat. No. 3,058,458. There have been attempts to build into portable monitoring devices the capability of monitoring more than one lead. For example, in commonly assigned U.S. Pat. No. 4,862,896, the two-electrode unit of the '507 patent was made adaptable to provide more than one lead by securing the electrodes in predetermined positions within the monitor housing so as to achieve an additional precordial lead or leads. Furthermore in commonly assigned U.S. Pat. No. 4,889,134, there is disclosed a portable heart monitor which embodies three electrodes so as to enable the user to obtain leads I, II, and III with the use of the device. Particularly, when the device is used in its diagnostic mode, it is desirable to provide a heart monitor which is capable of obtaining more than three leads.

BRIEF DESCRIPTION OF THE DRAWINGS

It is an object of the present invention to provide a portable heart monitor which has the capability of obtaining the electrical heart activity of an individual in a form capable of producing a twelve-lead electrocardiogram which includes leads I, II, III, AVR, AVL, AVF, $V_1$, $V_2$, $V_3$, $V_4$, $V_5$, and $V_6$. In accordance with the principles of the present invention, this objective is achieved by providing a heart monitor apparatus which includes an apparatus for obtaining electrical heart activity of an individual in a form capable of producing a twelve-lead electrocardiogram of an individual. The apparatus includes a portable electrode support having an array of six non-adhesive Wilson precordial electrodes fixed thereon at predetermined positions within the array which correspond with the Wilson precordial leads for the individual, a right arm electrode, a left arm electrode, a left leg electrode, and circuitry carried by the support in electrically connected relation to the electrodes for converting the electrical heart activity of the individual obtained by the electrodes into a form capable of producing a twelve-lead electrocardiogram. The right arm electrode, the left arm electrode, and the left leg electrode are constructed so as to be operable to be applied to the skin of the individual at locations such that the circuitry can be electrically operable to obtain leads I, II, III, AVR, AVL, and AVF therefrom. The array of six precordial electrodes and the support are constructed and arranged so as to be operable so that the array of six electrodes can be engaged with the skin of the chest of the individual and retained thereon in an operative relation applying human pressure to the support sufficient to retain the operative relation. A control for operating the circuitry is provided which is operable while the six precordial electrodes are retained in operative relation as aforesaid and the left arm electrode, the right arm electrode and the left leg electrode are applied as aforesaid, for a time sufficient to obtain electrical heart activity of the individual in a form capable of producing an electrocardiogram representative of leads I, II, III, AVR, AVL, AVF, $V_1$, $V_2$, $V_3$, $V_4$, $V_5$, and $V_6$.

Preferably, the support is of a size and shape to extend throughout the chest area containing the six Wilson precordial leads of the individual and to have the pressure applied by the individual to the support by the left arm and left hand. The support has opposed surfaces one of which constitutes an operatively interior surface on which the six precordial electrodes are fixed and the other of which constitutes an operatively exterior surface on which the individual applies pressure. The left arm electrode is non-adhesive and is fixed to the exterior surface of the support at the location thereof where pressure is applied to the support by the individual so as to enable the left arm electrode to be applied to the individual by engagement of the skin of the individual in an operative relation and retention of the operative relation by the pressure applied to the support by the individual.

Figure 1:
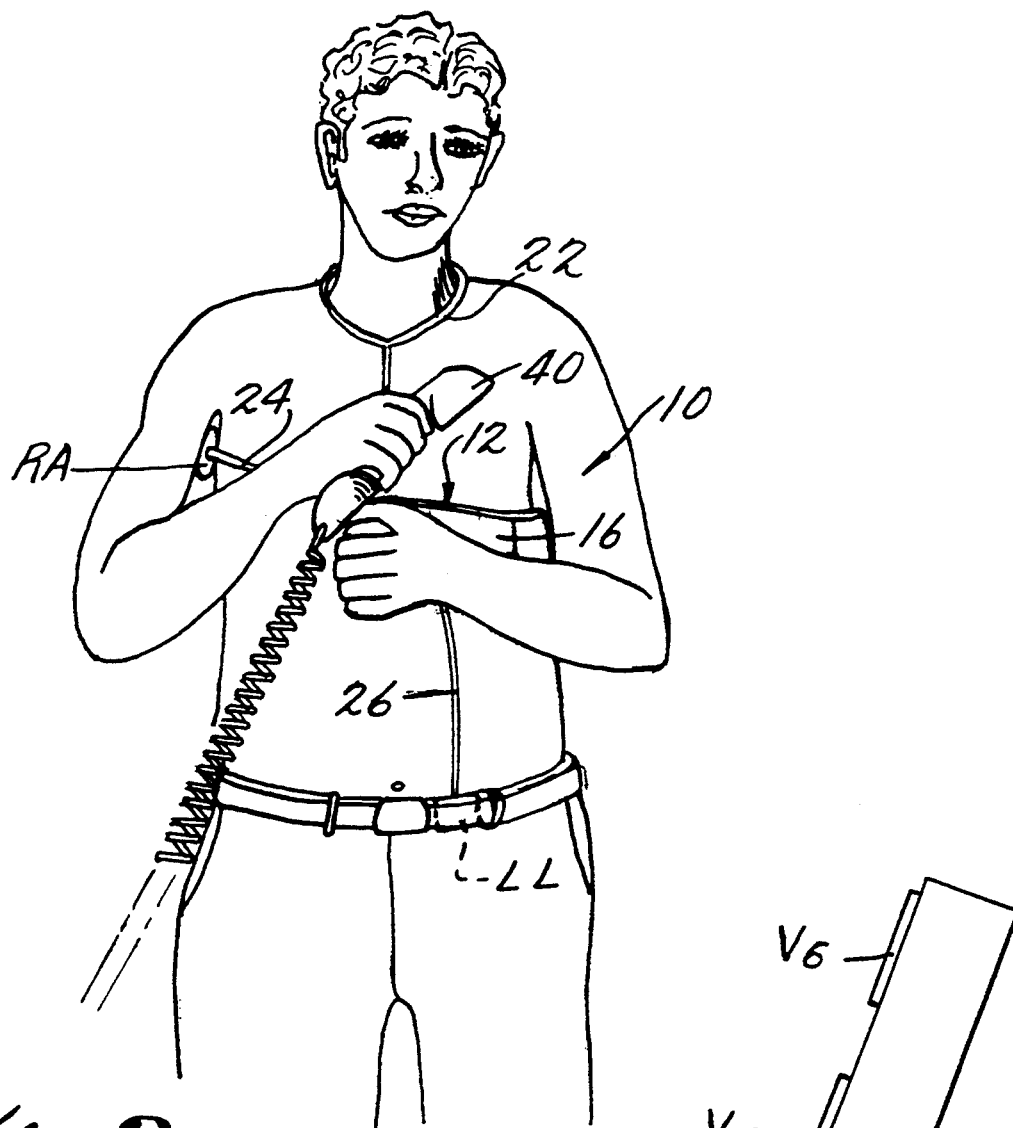

Preferably, the right arm electrode is of a non-adhesive material connected with the circuitry by a wire and is of a size and shape to be conveniently engaged with the skin to the right armpit of the individual in an operative relation and to be conveniently retained in an operative relation by pressure from the right arm of the individual. Preferably, the left leg electrode is of a non-adhesive material connected with said circuitry by a wire and is of a size and shape to be conveniently engaged with the skin of the waist of the individual in an operative position and retained in an operative relation by a garment extending around the waist of the individual.

Another object of the present invention is to provide a method of utilizing the heart monitor device of the type described. In accordance with one aspect of the present invention, this objective is obtained by providing a method of obtaining electrical heart activity of an individual in a form capable of producing a twelve-lead electrocardiogram of an individual which comprises the steps of applying the right arm electrode, the left arm electrode and the left leg electrode to the skin of the individual at locations such that the circuitry can be electrically operable to obtain leads I, II, III, AVR, AVL, and AVF therefrom and engaging the array of six precordial electrodes with the skin of the chest of the individual in an operative relation such that the circuitry can be electrically operable to obtain leads $V_1$, $V_2$, $V_3$, $V_4$, $V_5$, and $V_6$ therefrom and then operating the circuitry of the device for a time sufficient to obtain electrical heart activity of the individual in a form capable of producing an electrocardiogram representative of leads I, II, III, AVR, AVL, AVF, $V_1$, $V_2$, $V_3$, $V_4$, $V_5$, and $V_6$, while said six precordial electrodes are retained in skin-engagement by applying human pressure to the support sufficient to retain the operative relation and while the left arm electrode, the right arm electrode and the left leg electrode are applied as aforesaid.

Another object of the present invention is to provide a method of producing a twelve-lead electrocardiogram of an individual with the use of the aforesaid heart monitoring device used in the method aforesaid after which the obtained electrical heart activity of the individual is utilized to produce a twelve-lead electrocardiogram.

Preferably, the procedure for producing the twelve-lead electrocardiogram includes converting the obtained electrical heart activity of the individual within the circuitry of the device into audible signals indicative of the electrical heart activity of the individual, transmitting the audible signals over a telephone communication line to a remote location and utilizing the audible signals communicated over the telephone line to the remote location to produce the electrocardiogram by a strip chart recorder.

Alternatively, the electrocardiogram can be produced by a strip chart recorder carried by the support of the device or the obtained electrical heart activity of the individual can be stored in a memory in the circuitry and the memory is used to produce the twelve-lead electrocardiogram by a strip chart recorder.

Another object of the present invention is the provision of a heart monitoring device of the type described which is simple in construction, effective in operation, and economical to manufacture.

These and other objects of the present invention will become more apparent during the course of the following detailed description and appended claims.

The invention may best be understood with reference to the accompanying drawings wherein an illustrative embodiment is shown.

Figure 2:
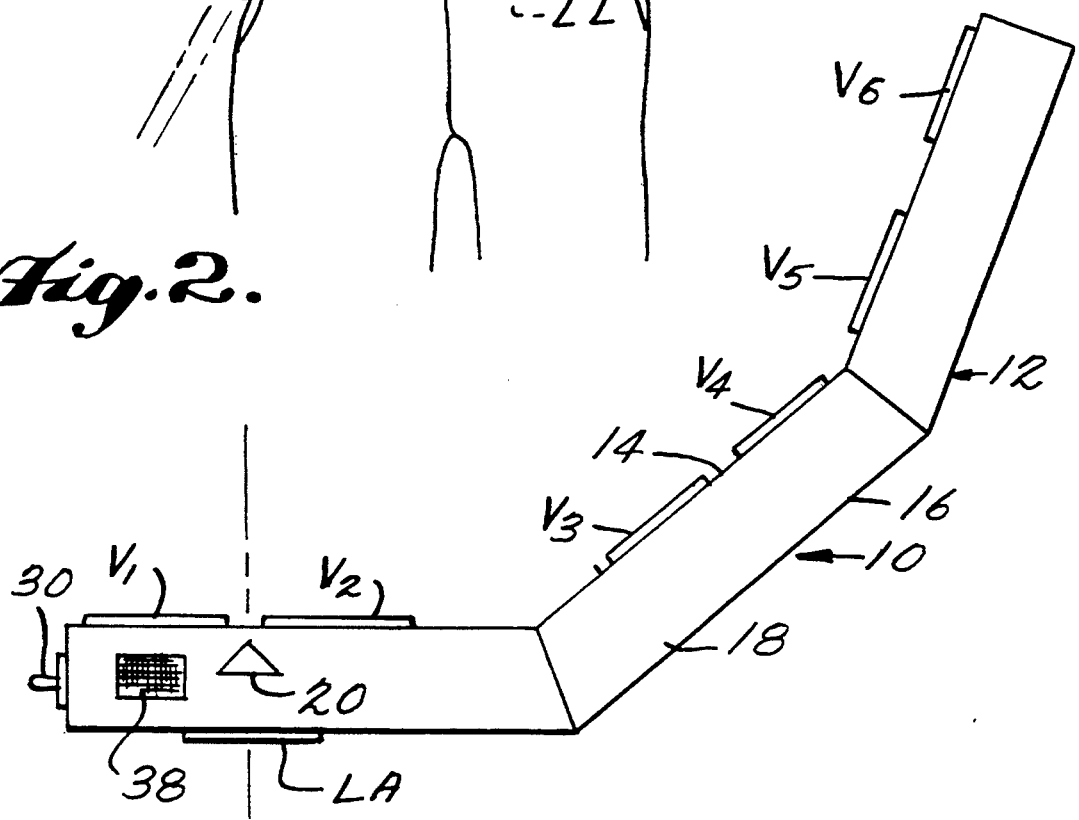
Figure 6:
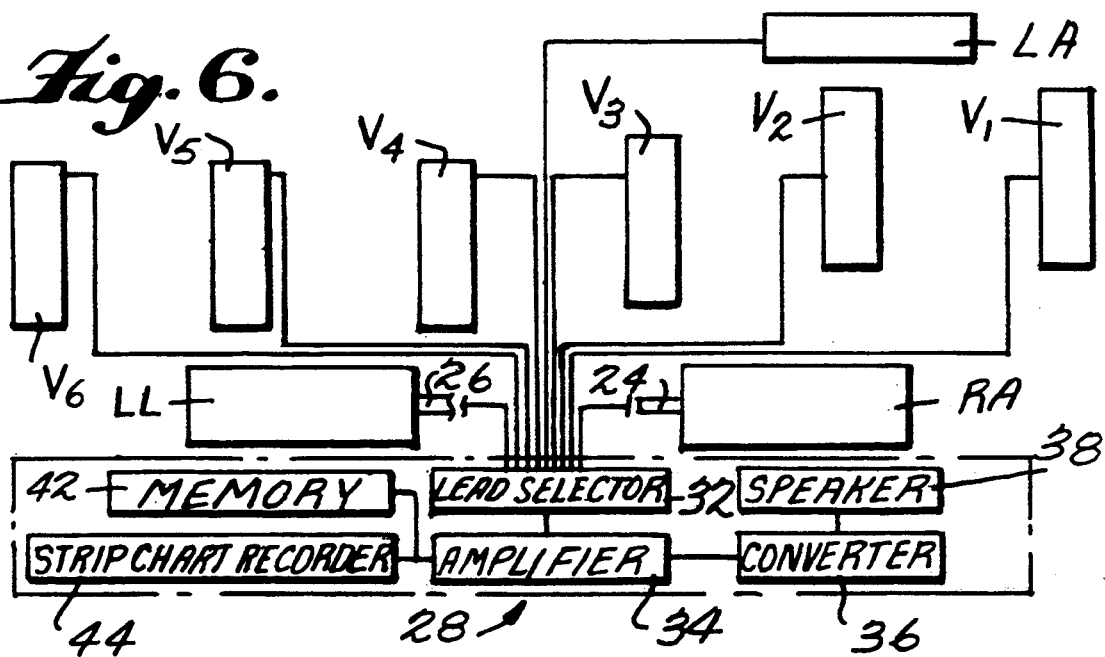
Figure 7:
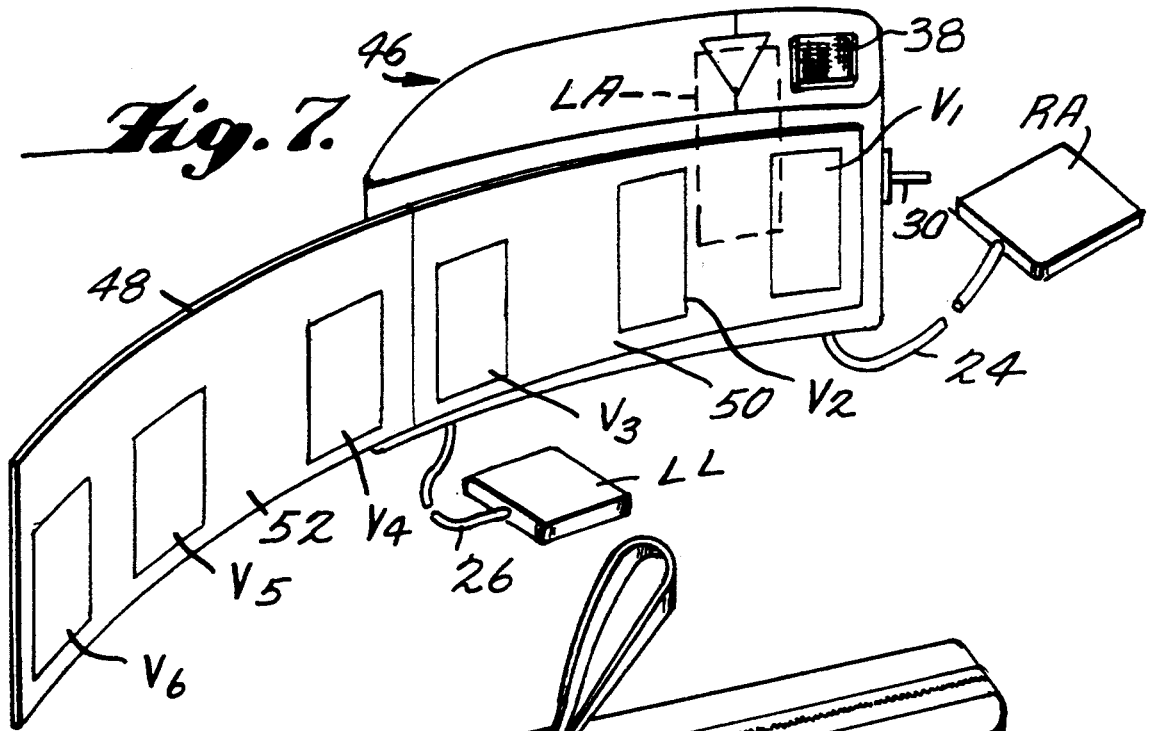
Figure 8:
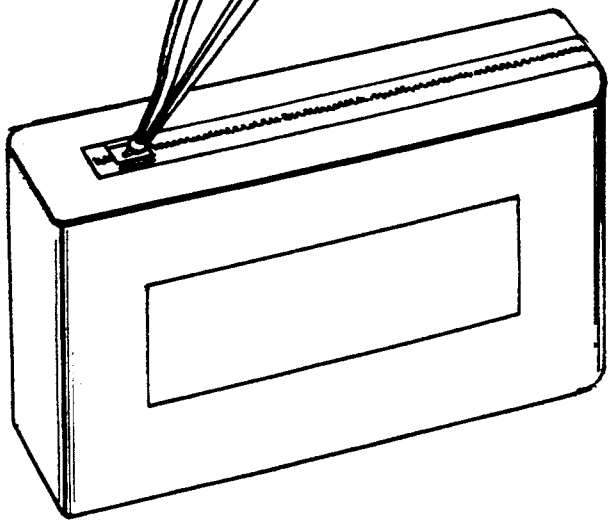

IN THE DRAWINGS:

FIG. 1 is a pictorial view showing an individual using the heart monitor apparatus of the present invention for transmitting the audible signals derived therein over a telephone line to a central source;

FIG. 2 is a top plan view of the heart monitor apparatus;

FIG. 3 is an elevational view of the operative exterior surface of the apparatus;

FIG. 4 is an elevational view of the operative interior surface of the apparatus;

FIG. 5 is a top and generally frontal perspective view of the apparatus;

FIG. 6 is a schematic view of the electric circuit of the apparatus;

FIG. 7 is a view similar to FIG. 5 showing a modified form of the apparatus; and FIG. 8 is a top and generally frontal perspective view of the apparatus shown in FIG. 7, encased within a carrying pouch.

DETAILED DESCRIPTION OF THE DRAWINGS

Referring now more particularly to FIG. 1 of the drawings, there is shown therein a heart monitor apparatus or device, generally indicated at 10, which embodies the principles of the present invention. The device 10 includes a portable electrode support, generally indicated at 12, which in its preferred embodiment as shown in FIGS. 1-5 is in the form of a hollow housing consisting of three sections interconnected rigidly in angular relation with respect to one another. The support or housing 12 is of a size and angular shape to generally conform with the chest of a user. As best shown in FIG. 2, the concave side of the angularly related sections of the hollow housing 12 constitute an operatively interior surface 14 of the housing which is adapted to engage toward the chest of the user, while the opposite side constitutes an operatively exterior surface 16 by which human pressure, preferably from the individual, can retain the hollow housing in operative engagement with the chest.

The portable electrode support 12 has fixed to the operative interior surface 14 thereof an array of six non-adhesive electrodes. The electrodes are designated by the reference characters $V_1$, $V_2$, $V_3$, $V_4$, $V_5$, and $V_6$, respectively, which correspond with the conventional six Wilson precordial leads also so designated. As shown, the six precordial leads are positioned on the operatively interior surface 14 of the hollow housing or electrode support 12 in positions which correspond with the six Wilson precordial leads of the individual. In this regard, it is contemplated that the array of electrodes on the electrode support 12 will be positioned basically to fit the individual that is to use the monitor. This can be done by manufacturing different sizes in a manner somewhat similar to the way shoes are manufactured, or the support could be simply made in three sizes, large, medium and small, and the electrodes can be fixedly mounted thereon, as by adhesive or suitable fasteners, in adjusted positions which are determined by fitting the support and electrodes to the individual. It would also be possible to provide for the six precordial electrodes to be adjustably fixedly mounted as by the use of "VELCRO" strips or the like although this mode is not preferred.

The electrodes themselves may be of any desired configuration. In the preferred embodiment shown in FIGS. 1-5, each one of the six precordial electrodes is non-adhesive and formed as indicated in the aforesaid '700 patent similar to the armpit electrodes disclosed therein. Basically, the electrodes are pads formed of carbon loaded thermoplastic material, as, for example, a vinyl resin. The pad-like configuration is utilized to enable the electrodes to be securely fastened to the support after the individual has been fitted. Where many different sizes may be produced, it would be desirable to print the electrodes on a substrate of conductive ink or the like.

As best shown in FIG. 2, an arrow 18 or other similar indicia is placed on an upper edge surface 20 of the support 12 to provide the user with a breast bone reference point which enables the user to orient the support and, hence, the six precordial electrodes fixed thereon, in proper horizontal adjusted position with respect to the individual chest. In addition, a lanyard 22 is connected with the support 20 for engagement around the neck of the individual. The lanyard 22 is adjusted in length so that, when it is fully extended, the support is disposed in its proper vertical adjusted position. When the support 12 is disposed in its proper vertical and horizontal adjusted position, the six precordial electrodes can be engaged with the skin of the chest of the individual in an operative relation wherein the six electrodes correspond with the six Wilson precordial leads for that individual. This engagement is preferably made with the left arm and left hand of the individual applying human pressure to the support 12 generally in the manner indicated in FIG. 1. The upper left arm in the elbow area of the individual engages the portion of the support carrying electrodes $V_5$ and $V_6$ and the lower left arm and left hand extend over the operatively exterior surface 18 so as to apply an even pressure to retain each of the six precordial electrodes in operative relation.

The monitoring device 10 also includes a left arm electrode, designated by the reference character LA, which is suitably fixed to the operatively exterior surface 16 of the electrode support 12. The left arm electrode is preferably nonadhesive and constructed like the six precordial electrodes. As shown, the left arm electrode LA is disposed in a position to be engaged with the skin of the palm of the individual in an operative relation as the individual engages the six precordial electrodes in their operative relation. The left arm electrode LA is retained in its operative relation by the human pressure applied to the support 12 by the individual.

It will be understood that, while the left arm electrode LA is shown and described above as having an operative relation with the skin of the palm, the location of the electrode on the support could be changed so that the operative relation could be with the skin of the forearm or any other part of the left arm of the individual which is applying pressure to the support 12 to retain the six precordial electrodes in their operative relation.

It will also be understood that, for monitoring devices which are to be particularly adapted for use in a diagnostic mode by paramedics or doctors, the left arm electrode may be adjustably mounted on the support, as by "VELCRO" or the like, in the same manner as aforesaid with respect to the six precordial electrodes. By providing a relatively long lead wire and rendering the left arm electrode adjustably mounted to the support with "VELCRO", the electrode can be removed from the support and placed in an operative relation under the individual's left armpit to be retained therein by the individual's left arm, thus enabling the paramedic or doctor to apply the human pressure to the support 12 sufficient to retain the six precordial electrodes in operative relation with the individual.

The monitoring device 10 also includes a right arm electrode which is designated by the reference character RA. This electrode is provided on the end of a wire 24 and preferably is non-adhesive and constructed like the armpit electrode of the aforesaid '700 patent, the disclosure of which is hereby incorporated by reference into the present specification. The right arm electrode RA is operable to be engaged with the skin of the right armpit of the individual in an operative relation and to be retained therein by the right arm of the individual.

The monitoring device 10 also includes a left leg electrode, which is designated by the reference character LL. The left leg electrode LL is preferably nonadhesive and constructed in a manner similar to the right arm electrode RA on the end of a lead wire 26. The left leg electrode LL is adapted to be engaged with the skin of the waist of the individual, generally somewhat on the left side in an operative relation, as shown in FIG. 1. The left leg electrode can be retained in operative relation by a garment extending around the waist. Alternatively, the left leg electrode LL can be held in operative relation within a fold of skin in the waist area when the individual is in a sitting position.

The monitoring device 10 also includes electrical circuitry, shown functionally in FIG. 6 and designated generally at 28. The circuitry 28 is suitably electrically connected with the nine electrodes thus far described and is suitably battery energized and operated by a control 30, such as a manual switch suitably mounted on the exterior of the support 12.

The circuitry 28 includes a lead selector 32, an example of which is disclosed in the aforesaid '458 patent, the disclosure of which is hereby incorporated by reference into the present specification. The lead selector automatically selects the combination of electrodes of the nine provided which will produce the twelve leads I, II, III, AVR, AVL, AVF, $V_1$, V, $V_3$, $V_4$, Vs, and $V_6$, in sequence when written for display in an electrocardiogram. The circuitry includes an amplifier component 34, a converter component 36, and a loud speaker 38. An example of these components of the circuitry is disclosed in the aforesaid '700 patent, the disclosure of which is hereby incorporated by reference into the present specification. Basically, the amplifier 34 amplifies the electric heart activity of the individual which is picked up by the electrodes selected by the lead selector 32. The converter 36 converts the output of the amplifier 34 into audible signals indicative of the electrical heart activity of the individuals which are emitted by the loud speaker.

FIG. 1 illustrates the method of using the monitoring device 10 by an individual in a heart program, such as disclosed in the aforesaid '260, '577, and '830 patents, each of which is hereby incorporated by reference into the present specification. In this use, the individual has applied the right arm electrode RA in operative relation within the right armpit, the left leg electrode LL in operative relation with the waist and is holding the support with his left arm and left leg so that the six precordial electrodes $V_1$, $V_2$, $V_3$, $V_4$, V, and $V_6$ are in operative relation with the individual's chest and the left arm electrode LA is in operative relation with the individual's left hand palm. When the control 30 is manually switched on by the individual, the circuitry 28 is operable to produce audible signals over the loud speaker 38 indicative of the electrical heart activity of the individual. FIG. 1 shows the individual holding the voice transmitting end of a telephone 40 to the loud speaker 38 so that the audible signals emitted thereby are transmitted over a telephone line to another telephone (not shown) at a remote source location where the received audible signals are utilized to produce a twelve-lead electrocardiogram as by a strip chart recorder (not shown).

It is within the contemplation of the present invention to include a memory component 42 in the circuitry. An example of a memory component is disclosed in the aforesaid '896 and '134 patents, the disclosures of which are hereby incorporated by reference into the present specification. The memory component 42 functions to store the output of the amplifier 34 in such a way that it can be retrieved on demand for use in producing a twelve-lead electrocardiogram on a strip chart recorder.

Finally, the circuitry 28 can include a strip chart recorder 44, which, like the circuitry mounted on a suitable circuit board, is suitably mounted within the hollow housing forming the portable electrode support 12. An example of a strip chart recorder which can be utilized is the recorder Model 9240LP marketed by MFE Instruments, Division of Stocker and Vale, Inc. The strip chart recorder 44 is placed in the circuitry 28 so that it can produce a twelve-lead electrocardiogram either from the output of the amplifier 34 or the memory 42.

Referring now more particularly to FIG. 7 and 8, there is illustrated therein a modification of the portable electrode support 12. Instead of providing the support 12 of the apparatus 10 as a rigid full extent hollow housing, the support can be constructed as shown in FIG. 7 in the form of a much smaller hollow housing 46 containing the circuitry 28 therein. As before, the breast bone indicating arrow 20, control 30 and loud speaker 38 are provided on the exterior of the smaller housing 46. However, in the case of the smaller housing 46, the support also includes a pad-like section 48 extending from the operatively interior surface 50 of the housing 46 at one end. The pad-like section is preferably flexible so that it can be made to conform to the skin of the chest when applied thereto. As shown, a first plurality of the six precordial electrodes, as, for example, $V_1$, $V_2$, and $V_3$, are fixed to the operatively interior surface 50 of the housing 46 and the remaining plurality of the six precordial electrodes, as, for example, $V_4$, $V_5$, and $V_6$, are fixed to an operatively interior surface 52 of the pad-like section 48. As before, the left arm electrode LL shown in dotted lines in FIG. 7 is fixed to the operatively exterior surface of the housing 46.

The advantage of the two-piece portable electrode support 46 and 48 of the apparatus shown in FIG. 7 is that pad-like section 48 can be folded over the electrodes LL and RA and over the housing 46 and engaged in a storage pouch 54 such as shown in FIG. 8. In this form, the device can be more easily carried and stored.

It thus will be seen that the objects of this invention have been fully and effectively accomplished. It will be realized, however, that the foregoing preferred specific embodiment has been shown and described for the purpose of this invention and is subject to change without departure from such principles. Therefore, this invention includes all modifications encompassed within the spirit and scope of the following claims.

What is claimed is:

1. A method of obtaining electrical heart activity of an individual in a form capable of producing a twelve-lead electrocardiogram of an individual with the use of a device including a portable electrode support having an array of six non-adhesive precordial electrodes fixed thereon at predetermined positions within the array which correspond with the Wilson precordial leads for the individual, a right arm electrode, a left arm electrode, a left leg electrode and circuitry for converting the electrical heart activity of the individual obtained by said electrodes into a form capable of producing a twelve-lead electrocardiogram, the method comprising applying the right arm electrode, the left arm electrode and the left leg electrode the skin of the individual at locations such that the circuitry can be electrically operable to obtain respective leads I, II, III, AVR, AVL, and AVF therefrom, utilizing an arm of the individual including at least the forearm and upper arm to engage the array of six precordial electrodes with the skin of the chest of the individual in an operative relation such that the circuitry can be electrically operable to obtain leads $V_1$, $V_2$, $V_3$, $V_4$, $V_5$, and $V_6$ therefrom, and operating the circuitry of said device for a time sufficient to obtain electrical heart activity of the individual in a form capable of producing an electrocardiogram representative of leads I, II, III, AVR, AVL, AVF, $V_1$, $V_2$, $V_3$, $V_4$, $V_5$, and $V_6$, while said six precordial electrodes are retained in skin-engagement by applying human pressure to the support sufficient to retain said operative relation and while said left arm electrode, said right arm electrode and said left leg electrode are applied as aforesaid.

2. A method as called for in claim 1, further utilizing the wrist and hand of said arm of the individual engage the array of six precordial electrodes with the skin of the chest.

3. A method as called for in claim 2 wherein pressure is applied to the support by utilizing the left arm, including the left wrist, left forearm and left hand of the individual to retain said array of six precordial electrodes in said skin-engagement with the chest.

4. A method as called for in claim 3 wherein the left arm electrode is a non-adhesive electrode and is fixed to said support on a location thereof where pressure is applied by the individual and wherein the left arm electrode is applied by engaging the same with the skin of the individual applying pressure on the support in an operative relation and retaining the left hand electrode in said operative relation by the pressure of the individual on the support.

5. A method as called for in claim 4 wherein the left leg electrode is a non-adhesive electrode and is applied by engaging the left leg electrode to the skin of the waist of the individual in an operative relation and retaining the left leg electrode in said operative relation by pressure applied exteriorly thereto.

6. A method as called for in claim 5 wherein exterior pressure is applied to said left leg electrode by a garment worn by the individual around the waist.

7. A method as called for in claim 5 wherein the right arm electrode is a non-adhesive electrode with the skin of the right armpit of the individual in an operative relation and retaining the right arm electrode in said operative relation by the individual applying pressure thereto with the right arm.

8. A method of producing a twelve-lead electrocardiogram of an individual with the use of a device including a portable electrode support having an array of six non-adhesive precordial electrodes fixed thereon at predetermined positions within the array which correspond with the Wilson precordial leads for the individual a right arm electrode, a left arm electrode, a left leg electrode and circuitry for converting the electrical heart activity data of the individual obtained by said electrodes into a form capable of producing a twelve-lead electrocardiogram, the method comprising applying the right arm electrode, the left arm electrode and the left leg electrode to the skin of the individual at locations such that the circuitry can be electrically operable to obtain leads I, II, III, AVR, AVL, and AVF therefrom, utilizing an arm of the individual including at least the forearm and upper arm to engage the array of six precordial electrodes with the skin of the chest of the individual in an operative relation such that the circuitry can be electrically operable to obtain leads $V_1$, $V_2$, $V_3$, $V_4$, $V_5$, and $V_6$ therefrom, operating the circuitry of said device for a time sufficient to obtain electrical heart activity of the individual in a form capable of producing an electrocardiogram representative of leads I, II, III, AVR, AVL, AVF, $V_1$, $V_2$, $V_3$, $V_4$, $V_5$, and $V_6$, while said six precordial electrodes are retained in skin-engagement by applying human pressure to the support sufficient to retain said operative relation and while said left arm electrode, said right arm electrode and said left leg electrode ar applied as aforesaid, and utilizing the obtained electrical heart activity of the individual to produce a twelve-lead electrocardiogram.

9. A method as called for in claim 8 wherein the procedure for producing the twelve-lead electrocardiogram includes converting the obtained electrical heart activity of the individual within said circuitry into audible signals indicative of the electrical heart activity of the individual, transmitting the audible signals over a telephone communication line to a remote location and utilizing the audible signals communicated over the telephone line to the remote location to produce said electrocardiogram by a strip chart recorder.

10. A method as called for in claim 8 wherein said electrocardiogram is produced by generating an electrical signal to a strip chart recorder carried by the support of the device.

11. A method as called for in claim 8 further comprising the steps of storing the obtained electrical heart activity of the individual in a memory in said circuitry and using said memory to produce said twelve-lead electrocardiogram by a strip chart recorder.

12. A method as called for in claim 8, utilizing the wrist and hand of said arm of the individual engage the array of six precordial electrodes with the skin of the chest.

13. An apparatus for obtaining electrical heart activity of an individual in a form capable of producing a twelve-lead electrocardiogram of an individual, said apparatus including an array of six non-adhesive precordial electrodes, support means for supporting said array of six non-adhesive precordial electrodes at predetermined positions within the array which correspond with Wilson precordial leads for the individual, said precordial electrodes each having an operative surface thereof generally facing in a first direction with respect to said supporting means, a right arm electrode, a left arm electrode, a left leg electrode, and circuitry means carried by said supporting means in electrically connected relation to said electrodes for converting the electrical heart activity of the individual obtained by said electrodes into a form capable of producing a twelve-lead electrocardiogram, said right arm electrode, said left arm electrode, and said left leg electrode being constructed so as to be operable to be applied to the skin of the individual at locations such that the circuitry means can be electrically operable to obtain leads I, II, III, AVR, AVL, and AVF therefrom, said supporting means presenting an exterior surface generally facing in a direction opposite to said first direction and adapted to have human pressure applied thereto, said supporting means being constructed and arranged in a manner which enables it to be manually held and moved towards the chest of the individual to engage said operative surface of said precordial electrodes with the skin of the chest, said apparatus requiring application of human pressure to said exterior surface transmitted through said supporting means to said precordial electrodes to retain said precordial electrodes in operative relation with the skin of the chest, and control means for operating said circuitry means while said six precordial electrodes are retained in said operative relation as aforesaid and said left arm electrode, said right arm electrode and said left leg electrode are applied as aforesaid, for a time sufficient to obtain electrical heart activity of the individual in a form capable of producing an electrocardiogram representative of leads I, II, III, AVR, AVL, AVF, $V_1$, $V_2$, $V_3$, $V_4$, $V_5$, and $V_6$.

14. An apparatus as called for in claim 13 wherein said supporting means is of a size and shape to extend throughout the chest area containing the six Wilson precordial leads of the individual and to have the pressure applied by the individual to the support means by the left arm and left hand, said supporting means having an operatively interior surface on which said six precordial electrodes are fixed.

15. An apparatus as called for in claim 14 wherein said left arm electrode is non-adhesive and is fixed to the exterior surface of said supporting means at the location thereof where pressure is applied to the supporting means by the individual so as to enable the left arm electrode to be applied to the individual by engagement by the skin of the individual in an operative relation and retention of the operative relation by the pressure applied to the supporting means by the individual.

16. An apparatus as called for in claim 15 wherein said supporting means includes a hollow housing within which said circuitry means is mounted.

17. An apparatus as called for in claim 16 wherein said hollow housing is rigid and of a size and shape to extend throughout the chest area containing the six Wilson precordial leads of the individual.

18. An apparatus as called for in claim 16 wherein said hollow housing is rigid and of a size and shape to receive a first plurality of said six precordial electrodes, said supporting means also including a flexible pad-like section connected therewith of a size to receive the remaining plurality of said six precordial electrodes, said flexible pad-like section being connected for movement between a storage position wherein the flexible pad section is wrapped around the hollow housing to enter therewith within a storage pouch and an operative position extending from said hollow housing so that when the first plurality of electrodes fixed to said hollow housing are retained in operative relation by pressure on said hollow housing from the left hand of the individual, the left arm of the individual can apply pressure to the flexible pad-like section to retain the remaining plurality of electrodes fixed thereto in operative relation.

19. An apparatus as called for in claim 16 wherein said right arm electrode is of a non-adhesive material connected with said circuitry means by a wire and is of a size and shape to be conveniently engaged with the skin to the right armpit of the individual in an operative relation and to be conveniently retained in said operative relation by pressure from the right arm of the individual.

20. An apparatus as called for in claim 19 wherein said left leg electrode is of a non-adhesive material connected with said circuitry means by a wire and is of a size and shape to be conveniently engaged with the skin of the waist of the individual in an operative position and retained in said operative relation by a garment extending around the waist of the individual.

21. An apparatus as called for in claim 16 wherein said circuitry means includes a loud speaker and is operable to convert the obtained electrical heart activity of the individual into audible signals emitted by said loudspeaker.

22. An apparatus as called for in claim 16 wherein said housing contains a strip chart recorder for producing the twelve-lead electrocardiogram from the obtained electrical heart activity of the individual.

23. An apparatus as called for in claim 16 wherein said circuitry means includes a memory within which the obtained electrical heart activity of the individual is stored.

24. An apparatus as called for in claim 16 wherein said supporting means has breast bone locating indicia thereon enabling the individual to locate the supporting means in an operative position with respect to the breast bone of the individual for determining the horizontal position of the operative relation of said six precordial electrodes.

25. An apparatus as called for in claim 24 wherein said support means has a lanyard connected therewith for extension around the neck of the individual, said lanyard having a portion thereof with a length defining the vertical position of the operative relation of said six precordial electrodes.

26. An apparatus as called for in claim 13 wherein said right arm electrode is of a non-adhesive material connected with said circuitry means by a wire and is of a size and shape to be conveniently engaged with the skin to the right armpit of the individual in an operative position and to be conveniently retained in said operative relation by pressure from the right arm of the individual.

27. An apparatus as called for in claim 13 wherein said left leg electrode is of a non-adhesive material connected with said circuitry means by a wire and is of a size and shape to be conveniently engaged with the skin of the waist of the individual in an operative position and retained in said operative relation by a garment extending around the waist of the individual.

28. An apparatus as called for in claim 13 wherein said circuitry means includes a loud speaker and is operable to convert the obtained electrical heart activity into audible signals emitted by said loudspeaker.

29. An apparatus as called for in claim 16 wherein said housing contains a strip chart recorder for producing the twelve-lead electrocardiogram from the obtained electrical heart activity of the individual.

30. An apparatus as called for in claim 13 wherein said circuitry means includes a memory within which the obtained electrical heart activity of the individual.

31. An apparatus as called for in claim 13 wherein said support means has breast bone locating indicia thereon enabling the individual to locate the supporting means in an operative position with respect to the breast bone of the individual for determining the horizontal position of the operative relation of said six precordial electrodes.

32. An apparatus as called for in claim 13 wherein said supporting means has a lanyard connected therewith for extension around the neck of the individual, said lanyard having a portion thereof with a length defining the vertical position of the operative relation of said six precordial electrodes.

33. An apparatus as called for in claim 13 wherein said left arm electrode is fixed to said supporting means in a position to be engaged with the skin of the palm of the left hand of the individual in said operative relation and retained in said operative relation by pressure applied to the supporting means by the left hand of the individual.

* * * * *